US00PP30428P3

(12) United States Plant Patent
Wang

(10) Patent No.: US PP30,428 P3
(45) Date of Patent: Apr. 23, 2019

(54) ***BROUSSONETIA* PLANT NAMED 'JINFENG'**

(50) Latin Name: ***Broussonetia* L'Hér. ex Vent.**
Varietal Denomination: Jinfeng

(71) Applicant: HENAN MINGPIN COLORIZED SEEDLING CO., LTD, Suiping, Henan (CN)

(72) Inventor: Huaming Wang, Henan (CN)

(73) Assignee: HENAN MINGPIN COLORIZED SEEDLING CO., LTD, Suiping, Henan (CN)

( * ) Notice: Subject to any disclaimer, the term of this patent is extended or adjusted under 35 U.S.C. 154(b) by 58 days.

(21) Appl. No.: 15/731,041

(22) Filed: Apr. 11, 2017

(65) Prior Publication Data

US 2017/0311502 P1 Oct. 26, 2017

(51) Int. Cl.
*A01H 5/00* (2018.01)
*A01H 5/12* (2018.01)

(52) U.S. Cl.
USPC ..... Plt./216
CPC ..... *A01H 5/12* (2013.01)

(58) Field of Classification Search
USPC ..... Plt./216
CPC ..... A01H 5/12; A01H 5/00
See application file for complete search history.

(56) References Cited

PUBLICATIONS

GTITM UPOVROM Citation for 'Jinfeng' as per CN PBR20150042; Sep. 8, 2015; 1 page.*

* cited by examiner

*Primary Examiner* — Kent L Bell

(57) ABSTRACT

'Jinfeng' is a distinctive variety of *Broussonetia* Plant, which is characterized by its color of leaves.

6 Drawing Sheets

Genus and species: *Broussonetia* L'Hér. ex Vent.
Variety denomination: 'Jinfeng'.

BACKGROUND OF THE INVENTION

The present invention relates to a new and distinct variety of *Broussonetia* plant, which is given the varietal denomination of 'Jinfeng'.

In April 2008, a mutated *Broussonetia* naturally occurring whole plant was found among *Broussonetia* seedlings in a nursery at Chuxu Village, Suiping County, Henan Province, China. Leaves of the mutated *Broussonetia* plant were golden in spring, yellow in summer and golden in autumn. However, leaves of other known seedlings in the same nursery were green. Since the main breeding material of this variety is branches, buds or rhizomes, branches of mutated were then grafted in spring and the mutated plant was reproduced by budding with xylem.

In April 2009, the mutated *Broussonetia* plant was grafted in the same nursery, and characteristics thereof were kept stable. In the nursery, except for some species of maple, there were no other varieties. The nursery has excellent land, smooth drainage, and no pollution sources around. The nursery is closed with only one entrance. Average summer maximum temperature at the nursery is 38 degrees Celsius, and average winter minimum temperature is −6 degrees Celsius. Annual average rainfall is 800 mm.

From 2010-2014, different generations were used for reproducing. No further mutation was observed. The distinct variety was healthy, and characteristics thereof were kept stable.

The new and distinct variety of *Broussonetia* plant is not commercially available.

SUMMARY OF THE NEW VARIETY

'Jinfeng' is a distinctive variety of *Broussonetia* plant with deciduous leaves, whose crown is extended. Bark of 'Jinfeng' is smooth, light gray or grayish brown, and without cracking. The whole plant contains milk-like sap. Young branches are densely covered with fine hairs. Single-leaves, which grow alternately and sometimes almost oppositely, are thick papery. The leaves are oval-shaped or wide oval-shaped with acute apices. Bases of the leaves are rounded, subcordate or skewed. The leaves have serrated margins, and have no crack or 3-5 cracks. Upper surfaces of the leaves are rough and covered with hard hairs. Lower surfaces of the leaves are covered with soft hairs. There are 7-8 pairs of lateral veins. In spring, the leaves are golden (RHS YELLOW 6C-A or YELLOW 7C-A) and top leaves are greyed-orange (RHS GREYED-ORANGE 163B-A). In summer, the leaves are yellow-green (RHS YELLOW-GREEN 150B-A or YELLOW-GREEN 144C-A). In autumn, the leaves turn back to golden and bright (RHS YELLOW 12D-A or YELLOW 13C-A). Petioles long 3-5 cm, and are densely covered with thick hairs. Stipules are ovate or oblong, and caduceus. Flowers are male with Catkin inflorescence, flowering from April to May.

BRIEF DESCRIPTION OF THE DRAWINGS

The accompanying colored photographs illustrate the overall appearance of the new and distinct variety of 'Jinfeng'. The descriptions disclosed herein are based upon observations of the plant growth.

DETAILED DESCRIPTION

Figure 1:
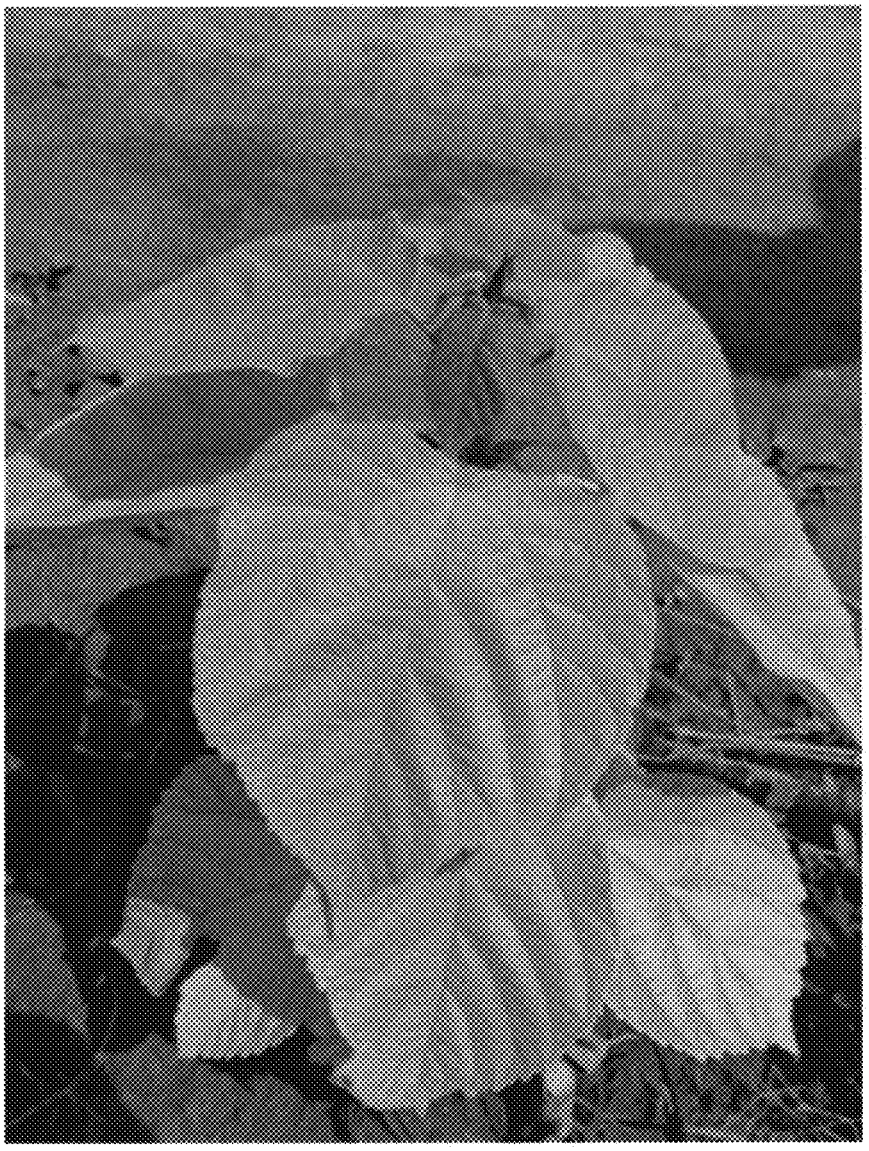
FIG. 1 is a color photograph of the new invention, 'Jinfeng', showing leaves of a 3-year plant on May 9, 2011.
Figure 2:
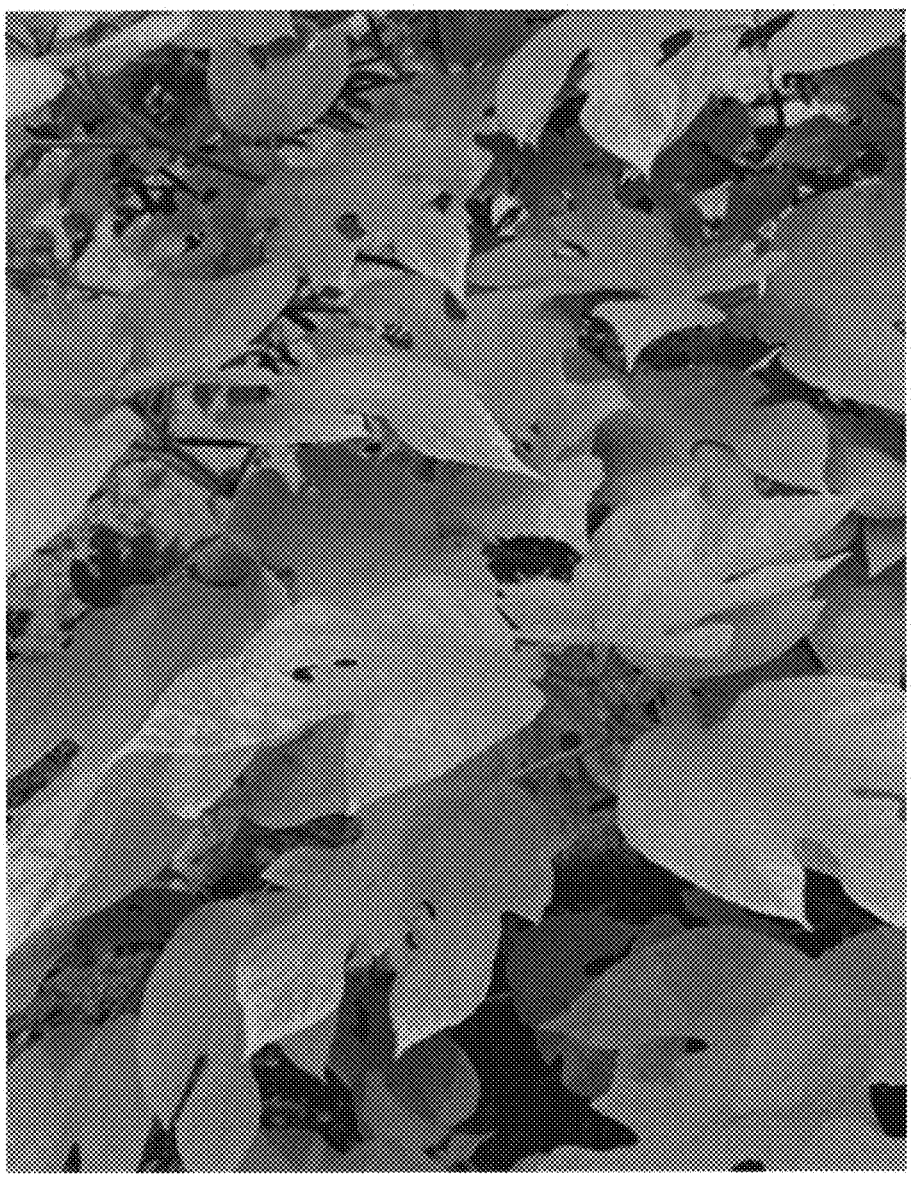
FIG. 2 is a color photograph of the new invention, 'Jinfeng', showing leaves of a 2-year plant on Sep. 17, 2011.
Figure 3:
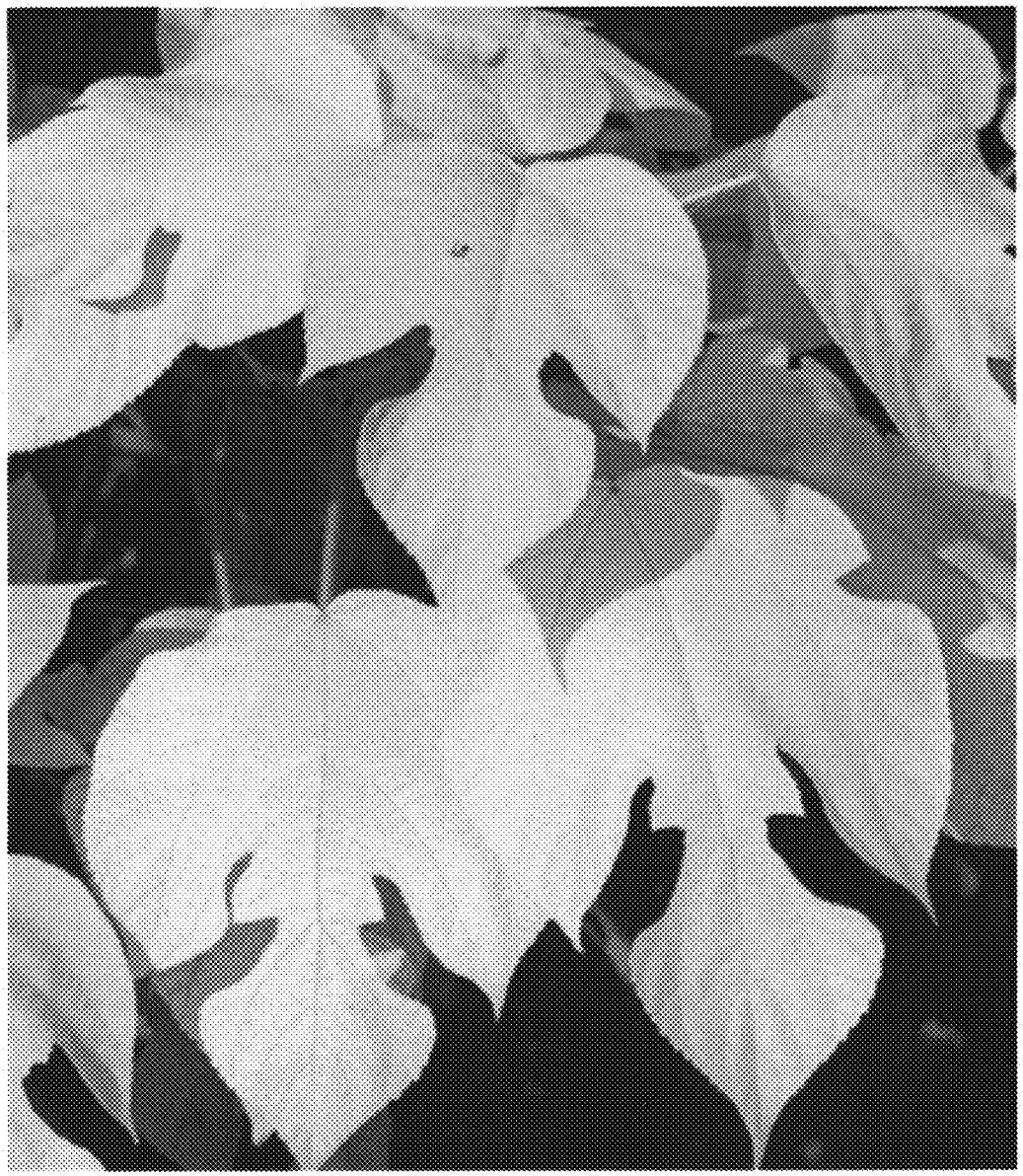
FIG. 3 is a color photograph of the new invention, 'Jinfeng', showing leaves of a 2-year plant on Oct. 13, 2011.
Figure 4:
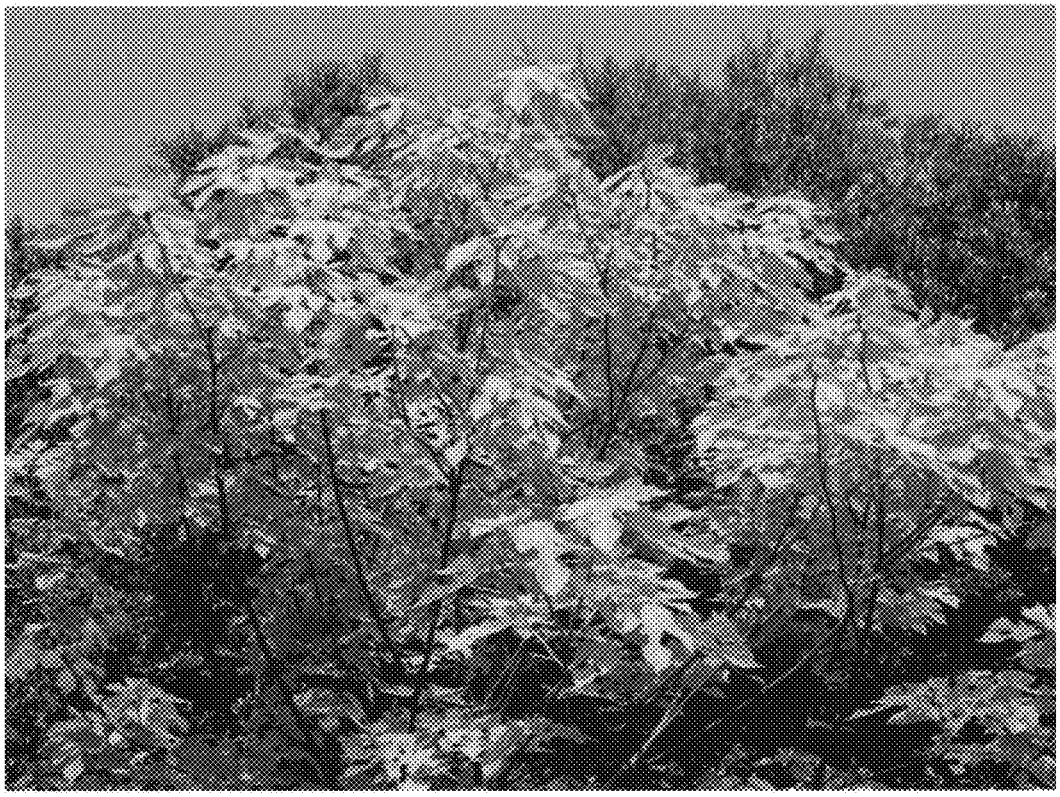
FIG. 4 is a color photograph of the new invention, 'Jinfeng', showing upward extending stem of a 4-year plant on Apr. 21, 2013.
Figure 5:
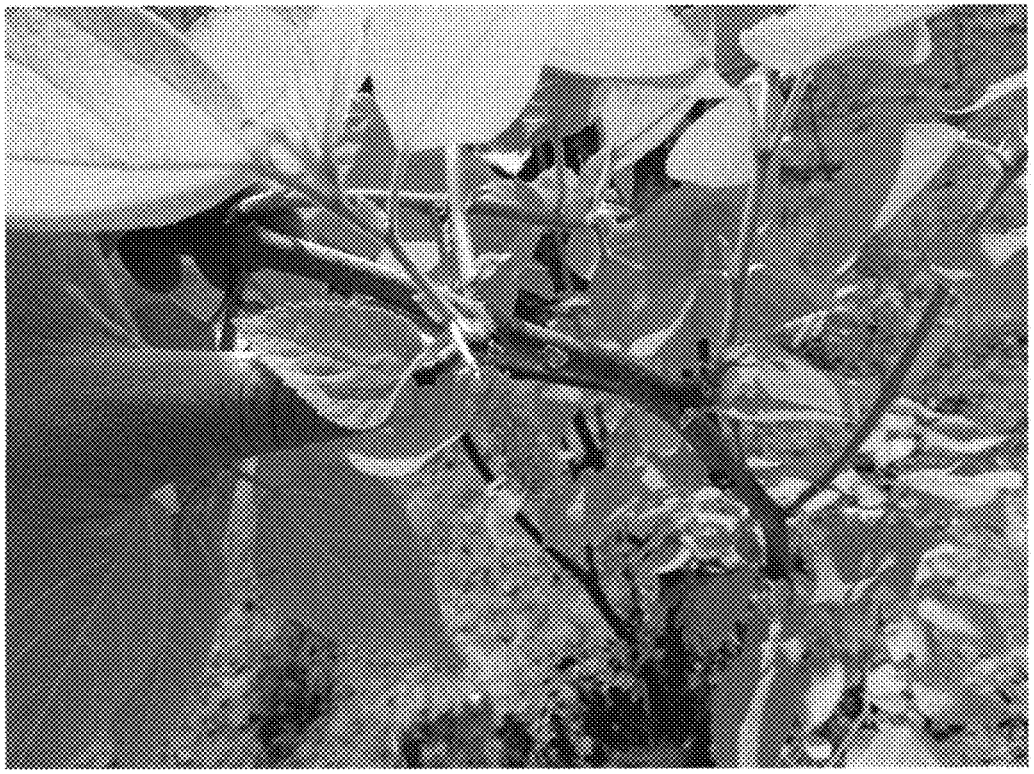
FIG. 5 is a color photograph of the new invention, 'Jinfeng', showing a 1-year plant in the field on May 3, 2012.
Figure 6:
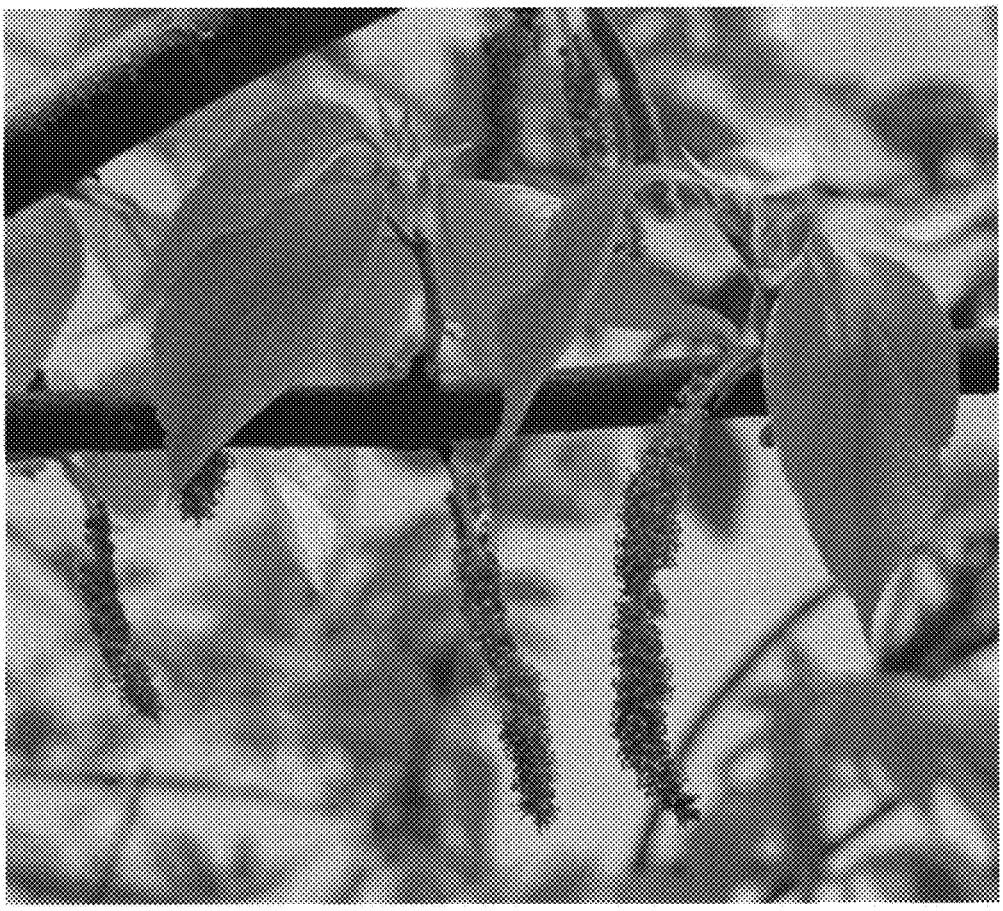
FIG. 6 is a color photograph of the invention, 'Jinfeng', showing the appearance of flowers without seeds of a 5-year plant on Apr. 21, 2014.

'Jinfeng' is a distinctive variety of *Broussonetia* plant with deciduous leaves, whose crown is extended. Bark of 'Jinfeng' is smooth, light gray or grayish brown, and without cracking. The whole plant contains milk-like sap. Young branches are densely covered with fine hairs. Single-leaves, which grow alternately and sometimes almost oppositely, are thick papery. The leaves are oval-shaped or wide oval-shaped with acute apices. Bases of the leaves are rounded, subcordate or skewed. The leaves have serrated margins, and have no crack or 3-5 cracks. Upper surfaces of the leaves are rough and covered with hard hairs. Lower surfaces of the leaves are covered with soft hairs. There are 7-8 pairs of lateral veins. In spring, the leaves are golden (RHS YELLOW 6C-A or YELLOW 7C-A) and top leaves are greyed-orange (RHS GREYED-ORANGE 163B-A). In summer, the leaves are yellow-green (RHS YELLOW-GREEN 150B-A or YELLOW-GREEN 144C-A). In autumn, the leaves turn back to golden and bright (RHS YELLOW 12D-A or YELLOW 13C-A). Petioles long 3-5 cm, and are densely covered with thick hairs. Stipules are ovate or oblong, and caduceus. Flowers are male with Catkin inflorescence, flowering from April to May.

'Jinfeng' is a distinctive variety of *Broussonetia* plant, which is able to grow in north, center, southwest, and northwest of China, mainly in the Yellow River area, the Yangtze River area and the Pearl River Basin area.

'Jinfeng' is a strong phototropism tree species, whose adaptability is particularly strong. The plant has strong resistance to dry-cold and dry and damp-hot climates, and is able to grow in acidic soil, neutral soil and limestone mountain area due to resistance to drought and barren. The plant grows well at both waterside and wetlands. Roots of the plant are shallow and lateral, which are widely distributed and rapidly grow. 'Jinfeng' has strong abilities in budding and tillering, with strong resistance to pruning and pollution.

Reproducing methods of 'Jinfeng' are mainly graft and cottage. For grafting, *Broussonetia* plant is used as a rootstock. In spring, cleft or budding with xylem should be adapted for propagating. In summer, budding is used for propagating. For cottage, young summer branches are mainly used.

Specifically, branch-graft in spring has a highest survival rate. Every year, in March or before 'Jinfeng' is budded, branches born that year are selected. The branches are cut into about 5 cm long, and bottoms are chamfered, which contains 2-3 buds. Next, the rootstock (with a roughness of between 0.7-1) is cut off flatly, and then vertically cut near one side. The graft material is aligned with one side of the rootstock layer, clamped, and wrapped with a graft plastic film, wherein the buds are left outside. After new leaves are grown, green branches of common species are removed from the rootstocks, so as to the branches of 'Jinfeng' grow rapidly. After the plant grows to 2 meters high, it is planted at a row spacing of 3 meters * 4 meters. After 3-4 years, trunks of 'Jinfeng' can grow to a diameter of 8 cm and can be used in greening of parks or scenic spots.

'Jinfeng' can be cultivated and rapidly grows in both spring and autumn. During growth, trimming is needed. The plant is not suitable for growing at low areas which are likely to suffer water logging.

'Jinfeng' can be cultivated in most parts of China, which prefers strong sunlight and is resistant to drought. 'Jinfeng' is not resistant to water and humidity. The roots are shallow but strong in germination, which is resistant to pruning, and highly adaptable to different type of soil.

'Jinfeng' rarely suffers from pests and diseases. However, in some particular regions having trunk-attacking pests such as longhorned beetles and jewel beetles, preventing is needed.

TABLE 1 comparison between 'Jinfeng' and similar species.

| similar species | features of similar species | features of 'Jinfeng' |
|---|---|---|
| 1 paper mulberry | dioecism | male |
| | green young leaves | yellow |
| | green mature leaves | yellow-green in summer, golden in autumn |
| 2 'Jinyang' | female | male |
| | smooth upper surface of leaf | rough |
| | no hair or nearly no hair on upper surface of leaf | densely cover by hairs |

These features and other characteristics of the plant are apparent from the figures.

What is claimed is:

1. A new and distinct variety of *Broussonetia* Plant named 'Jinfeng', substantially as described and illustrated.

* * * * *